United States Patent [19]

Billeb et al.

[11] Patent Number: 5,347,054
[45] Date of Patent: Sep. 13, 1994

[54] PROCESS FOR PREPARING AROMATIC ALDEHYDES

[75] Inventors: Gilbert Billeb, Kelkheim/Taunus; Peter Burg, Kriftel/Taunus, both of Fed. Rep. of Germany

[73] Assignee: Hoechst Aktiengesellschaft, Frankfurt am Main, Fed. Rep. of Germany

[21] Appl. No.: 156,451

[22] Filed: Nov. 23, 1993

[30] Foreign Application Priority Data

Nov. 26, 1992 [DE] Fed. Rep. of Germany ....... 4239737

[51] Int. Cl.⁵ .................................................. C07C 45/42
[52] U.S. Cl. ..................................... 568/437; 568/426
[58] Field of Search .................... 568/437, 425, 426

[56] References Cited

FOREIGN PATENT DOCUMENTS 2044832  3/1971  Fed. Rep. of Germany ...... 568/437
0248640 12/1985  Japan ................................ 568/437

OTHER PUBLICATIONS

Database WPI, Week 8604, Derwent Publications Ltd., London, GB; AN 86-025603 & JP-A-60 248 640 (Hodogaya Chem. Ind. KK) Dec. 9, 1985.
Database WPI, Week 8550, Derwent Publications Ltd., London, GB; AN 85-313611 & JP-A-60 218 349 (Hodogaya Chem. Ind. KK) Nov. 1, 1985.

*Primary Examiner*—Werren B. Lone

[57] ABSTRACT

A process for preparing aromatic aldehydes of the formula (1)

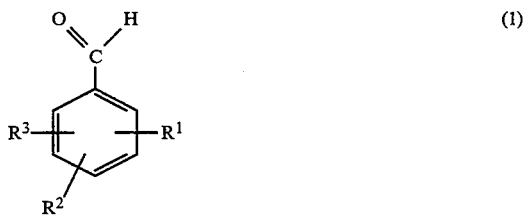

in which $R^1$, $R^2$, $R^3$ independently of one another are H, F, Cl or Br, by hydrolyzing a dichloromethyl-substituted benzene of the formula (2)

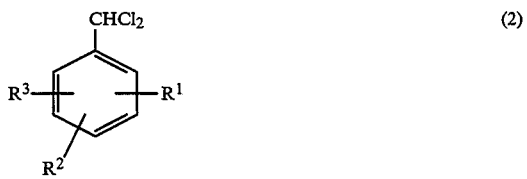

in which $R^1$, $R^2$, $R^3$ have the abovementioned meanings with a from about 1 to about 50% strength aqueous solution of one or more zinc salts of the formula (3)

$$ZnX_n \qquad (3)$$

in which X is F, Cl, Br, I, OH or $SO_4$, and n is, depending on the anion X, the number 1 or 2, at temperatures of from about 70° to about 160° C.

9 Claims, No Drawings

PROCESS FOR PREPARING AROMATIC ALDEHYDES

Aromatic aldehydes are important starting materials for many compounds, for example in the area of crop protection agents and pharmaceuticals.

Aromatic aldehydes are generally prepared by saponification of the corresponding dichloromethyl-substituted aromatics with water in the presence of acids or metal salts in accordance with the reaction equation

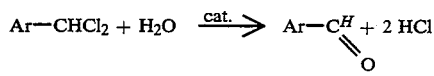

(cf. Houben-Weyl, VII, p. 211 ff.).

This reaction is usually carried out by initially charging the dichloromethyl-substituted aromatic and the catalyst at elevated temperature and metering in water. After the reaction has ended, the mixture is either directly distilled, in which case the catalyst ends up in the distillation residue, or it is subjected to aqueous workup, in which case the catalyst ends up in the waste water.

An exception is a process (BE 767 990) in which iron(III) chloride is used as the catalyst. In this process, after workup with a base, the iron is precipitated as oxide or hydroxide and removed. However, even in this process the catalyst must finally be disposed of or be separately worked up. Furthermore, the use of iron salts which are potential Friedel-Crafts catalysts may lead to undesired secondary reactions (Friedel-Crafts reactions, polymerizations) which can often proceed in an uncontrolled manner.

There is therefore, with a view to an environmentally friendly and economical method of production, a need for an improved process for preparing substituted or unsubstituted benzaldehydes which does not have the abovementioned disadvantages and in which a catalyst system is used which can be separated off after the reaction and recycled with minimum effort. In the literature there are no directions for carrying out the reaction in such a way.

It has now been surprisingly found that aromatic aldehydes of the formula (1)

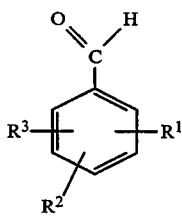

in which $R^1$, $R^2$, $R^3$ independently of one another are H, F, Cl or Br, preferably H, F or Cl, can be prepared in an advantageous manner continuously or batchwise by hydrolyzing a dichloromethyl-substituted benzene of the formula (2)

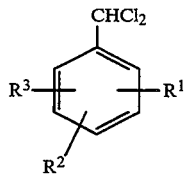

in which $R^1$, $R^2$, $R^3$ have the abovementioned meanings with a from about 1 to 50% strength, preferably a from about 1.1 to 15% strength, aqueous solution of one or more zinc salts of the formula (3)

$$ZnX_n \quad (3)$$

in which X is F, Cl, Br, I, OH or $SO_4$, preferably Cl, Br, OH or $SO_4$, and n is, depending on the anion X, the number 1 or 2, at temperatures of from about 70° to about 160° C., preferably from about 100° to about 140° C.

Further details of the process of the invention are:

The benzal chloride of the stated formula (2) is initially charged at the abovementioned temperatures. The aqueous catalyst solution is then metered in, the amount of the solution being determined by the stoichiometric consumption of water and the optional addition of an excess up to 100% being possible. After complete conversion of the substituted or unsubstituted benzal chloride the reaction mixture is extracted with water, the amount of water being calculated so that an at least 1% strength solution of the zinc salt is obtained. Preferably, the amount of water used for the extraction in one or more portions is the same as that stoichiometrically consumed during the reaction. The resulting zinc salt-containing aqueous phase is recirculated and re-used for saponification. The organic phase is subsequently free of zinc and hydrochloric acid, which makes the subsequent workup by distillation very much easier and drastically reduces the amount of distillation residue.

In the continuous operation of the process the saponification of the compounds of the stated formula (1) is carried out continuously in a cascade of stirred reactors and the resulting reaction mixture is continuously treated with water in the manner described above and the resulting zinc salt-containing aqueous solution is continuously recirculated. The organic phase is worked up in the above-described manner by distillation.

The process is marked in particular by high environmental friendliness, since no (heavy) metal-containing waste waters or distillation residues occur. Compared with the conventional processes, catalyst consumption is drastically reduced, which leads to considerable cost savings.

The fact that in the process of the invention the aqueous zinc salt solutions proved so effective in the desired sense was so surprising because these solutions were described in the literature (J. Legocki et al., Pr. Inst. Przem. Org. 1974, 6, 1–9) as catalytically inactive. Accordingly there are in the literature no examples of and no directions for saponification of dichloromethylsubstituted aromatics with aqueous zinc salt solutions.

The examples below illustrate the process of the invention without limiting it to them.

EXAMPLE 1

195.3 g (1.0 mol) of 2-chlorobenzal chloride are initially charged at 120° C. At this temperature 20 ml (21.8 g, 1.09 mol of water) of a 10% strength aqueous zinc chloride solution are metered in over a period of 5 hours. The mixture is stirred for a further 30 minutes at 120° C. After cooling to room temperature the reaction mixture is extracted with 1×10 ml and 2×5 ml of water. The organic phase is subsequently free of chloride and is worked up by distillation. 136.0 g (97% of theoretical) of 2-chlorobenzaldehyde (b.p.: 90° C./16 torr) with a purity of >99.9% are obtained. The combined aqueous phases (20 ml, 22.0 g) are used in Example 2 as catalyst solution.

EXAMPLE 2

195.3 g (1.0 mol) of 2-chlorobenzal chloride are saponified analogously to Example 1, the aqueous extract from Example I (20 ml) being used in place of fresh zinc chloride solution. After working up analogously to Example 1, 136.3 g (97% of theoretical) of 2-chlorobenzaldehyde with a purity of >99.9% are obtained. 20 ml of aqueous extract are obtained, which are again used in a saponification. A total of 5 saponification cycles are carried out, in each case the aqueous extract from the preceding experiment being used:

| Cycle | Yield [g] | Yield [%] |
|---|---|---|
| I | 136.3 | 97.0 |
| II | 135.5 | 96.4 |
| III | 137.0 | 97.5 |
| IV | 136.0 | 96.8 |
| V | 135.5 | 96.4 |

EXAMPLE 3

The saponification of 2-chlorobenzal chloride (charge: 195.3 g) is carried out analogously to Examples 1 and 2 with 5% strength aqueous zinc chloride solution, the results below being obtained:

| Cycle | Yield [g] | Yield [%] |
|---|---|---|
| I | 135.5 | 96.4 |
| II | 134.5 | 95.7 |
| III | 136.5 | 97.1 |
| IV | 137.0 | 97.5 |
| V | 135.5 | 96.4 |

EXAMPLE 4

The saponification of 4-chlorobenzal chloride (charge: 195.3 g) is carried out analogously to Examples 1 and 2 at 100° C. with 10% strength aqueous zinc chloride solution. After distillation of the organic phase at 80° C./10 torr the results below are obtained:

| Cycle | Yield [g] | Yield [%] |
|---|---|---|
| I | 135.0 | 96.1 |
| II | 136.0 | 96.8 |
| III | 134.5 | 95.7 |
| IV | 135.2 | 96.2 |
| V | 137.,0 | 97.5 |

EXAMPLE 5

The saponification of 2-chloro-6-fluorobenzal chloride (charge: 213.3 g) is carried out analogously to Examples 1 and 2 at 140° C. with 10% strength aqueous zinc chloride solution. After distillation of the organic phase at 90° C./10 torr the results below are obtained:

| Cycle | Yield [g] | Yield [%] |
|---|---|---|
| I | 150.5 | 95.0 |
| II | 152.1 | 96.0 |
| III | 151.0 | 95.3 |
| IV | 152.9 | 96.5 |
| V | 153.5 | 95.9 |

EXAMPLE 6

4-Fluorobenzal chloride (charge: 178.8 g) is saponified analogously to Example 4 at 100° C. with 10% strength aqueous zinc chloride solution. After distillation at 70° C./10 torr the results below are obtained:

| Cycle | Yield [g] | Yield [%] |
|---|---|---|
| I | 116.5 | 94.0 |
| II | 118.4 | 95.5 |
| III | 119.6 | 96.5 |
| IV | 117.8 | 95.0 |
| V | 120.0 | 96.8 |

EXAMPLE 7

195.3 g (1.0 mol) of 2-chlorobenzal chloride are reacted analogously to Examples 1 and 2 with 10% strength aqueous Zn(OH)$_2$ solution. No results significantly different to those in Example 2 are obtained.

What is claimed is:

1. A process for preparing aromatic aldehydes of the formula (1)

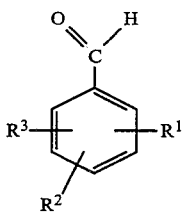

(1)

in which $R^1$, $R^2$, $R^3$ independently of one another are H, F, Cl or Br, which comprises hydrolyzing a dichloromethyl-substituted benzene of the formula (2)

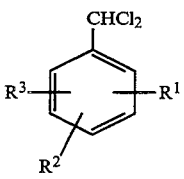

(2)

in which $R^1$, $R^2$, $R^3$ have the abovementioned meanings with a from about 1 to about 50 % strength aqueous solution of one or more zinc salts of the formula (3)

$$ZnX_n \qquad (3)$$

in which X is F, Cl, Br, I, OH or SO$_4$, and n is, depending on the anion X, the number 1 or 2, at temperatures of from about 70° to about 160° C.

2. The process as claimed in claim 1, wherein $R^1$, $R^2$, $R^3$ in the formulae (1) and (2) are H, F or Cl.

3. The process as claimed in claim 1, wherein X in the formula (3) is Cl, Br, OH or $SO_4$.

4. The process as claimed in claim 1, wherein hydrolysis is carried out at temperatures from about 100° to about 140° C.

5. The process as claimed in claim 1, wherein hydrolysis is carried out with a from about 1.1 to about 15% strength aqueous solution of one or more zinc salts of the formula (3) given in claim 1.

6. The process as claimed in claim 1, wherein a crude saponification mixture results from said hydrolyzing step, and said crude saponification mixture is extracted with water and the resulting aqueous zinc salt-containing solution is recirculated and re-used as said about 1 to about 50% strength aqueous solution.

7. The process as claimed in claim 1, wherein a crude saponification mixture results from said hydrolyzing step, and said crude saponification mixture is extracted with an amount of water calculated so that an at least 1% strength solution of the zinc salt is obtained.

8. The process as claimed in claim 1, wherein a crude saponification mixture results from said hydrolyzing step is extracted with an amount of water which is generally the same as that which is stoichiometrically used up during the hydrolyzing step.

9. The process as claimed in claim 1, wherein the hydrolysis step is carried out continuously in a cascade of stirred reactors, the reaction mixture obtained is treated continuously with water and the resulting zinc salt-containing aqueous solution is continuously recirculated.

* * * * *